United States Patent
Kaiser et al.

(10) Patent No.: US 7,027,857 B2
(45) Date of Patent: Apr. 11, 2006

(54) METHOD AND SYSTEM FOR IMPROVED MEASUREMENT OF T-WAVE ALTERNANS

(75) Inventors: Willi Kaiser, Emmendingen (DE); Martin Findeis, Freiburg (DE)

(73) Assignee: The General Electric Company, Schenectady, NY (US)

( * ) Notice: Subject to any disclaimer, the term of this patent is extended or adjusted under 35 U.S.C. 154(b) by 520 days.

(21) Appl. No.: 10/367,028

(22) Filed: Feb. 14, 2003

(65) Prior Publication Data

US 2004/0162498 A1 Aug. 19, 2004

(51) Int. Cl.
*A61B 5/04* (2006.01)
(52) U.S. Cl. ..................... 600/515; 600/509
(58) Field of Classification Search ............... 600/515, 600/516, 517, 518
See application file for complete search history.

(56) References Cited

U.S. PATENT DOCUMENTS

| | | | |
|---|---|---|---|
| 5,148,812 A | | 9/1992 | Verrier et al. |
| 5,713,367 A | * | 2/1998 | Arnold et al. .............. 600/517 |
| 5,908,393 A | | 6/1999 | Albrecht et al. |
| 6,169,919 B1 | | 1/2001 | Nearing et al. |
| 6,453,191 B1 | | 9/2002 | Krishnamachari |
| 2003/0060724 A1 | * | 3/2003 | Thiagarajan et al. ........ 600/515 |

* cited by examiner

*Primary Examiner*—Robert E. Pezzuto
*Assistant Examiner*—Joy Patel
(74) *Attorney, Agent, or Firm*—Andrus, Sceales, Starke & Sawall, LLP

(57) ABSTRACT

A method and system for improved measurement of T-wave alternans in an ECG signal is disclosed. The method and system comprise receiving digitized ECG data including a plurality of alternating consecutive odd and even beats, calculating a variability for at least one odd or even beat, and excluding certain beats from T-wave alternans measurements according to an exclusion procedure.

35 Claims, 5 Drawing Sheets odd  even  odd  even  odd  even  odd  even

PRECORDIAL ECG

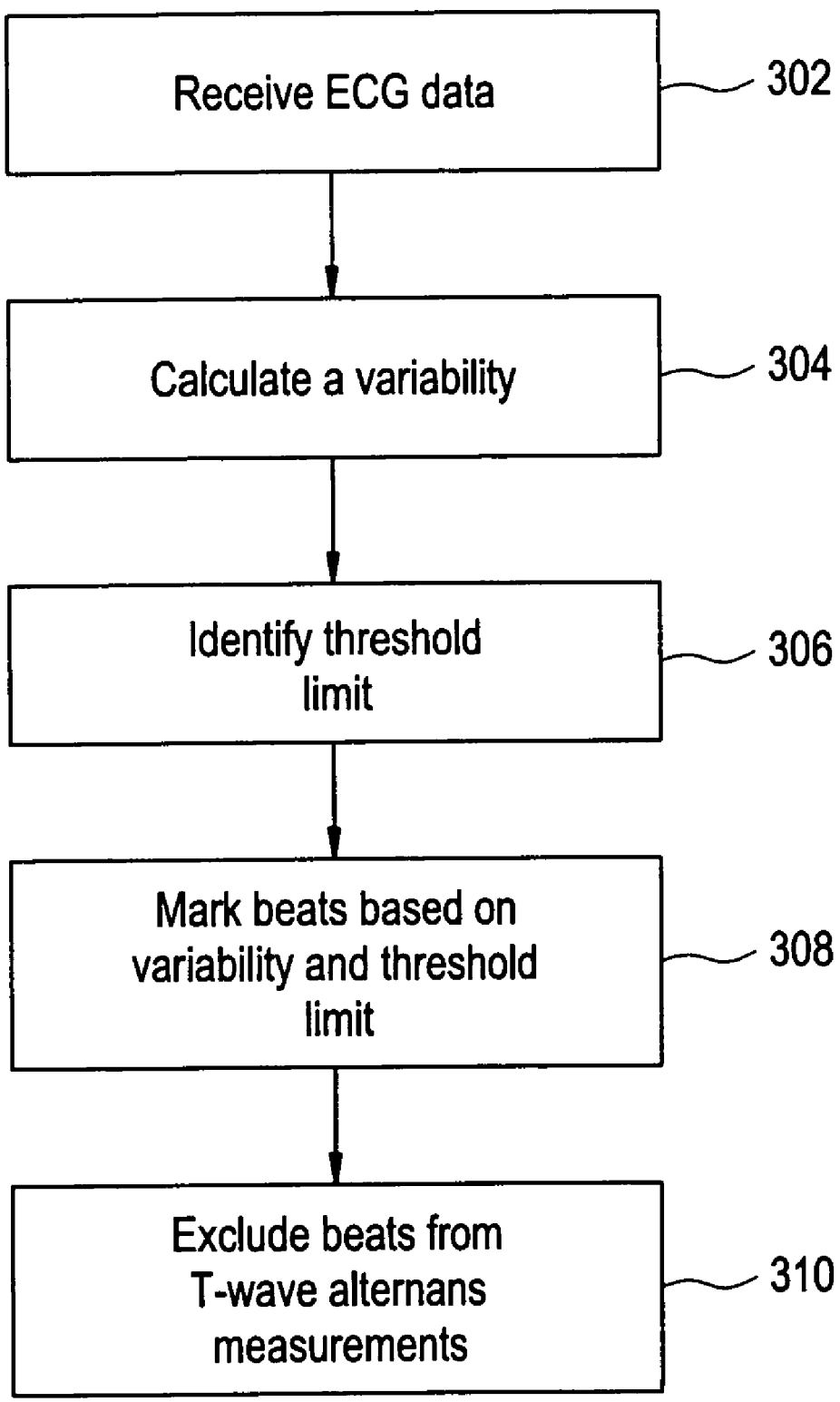

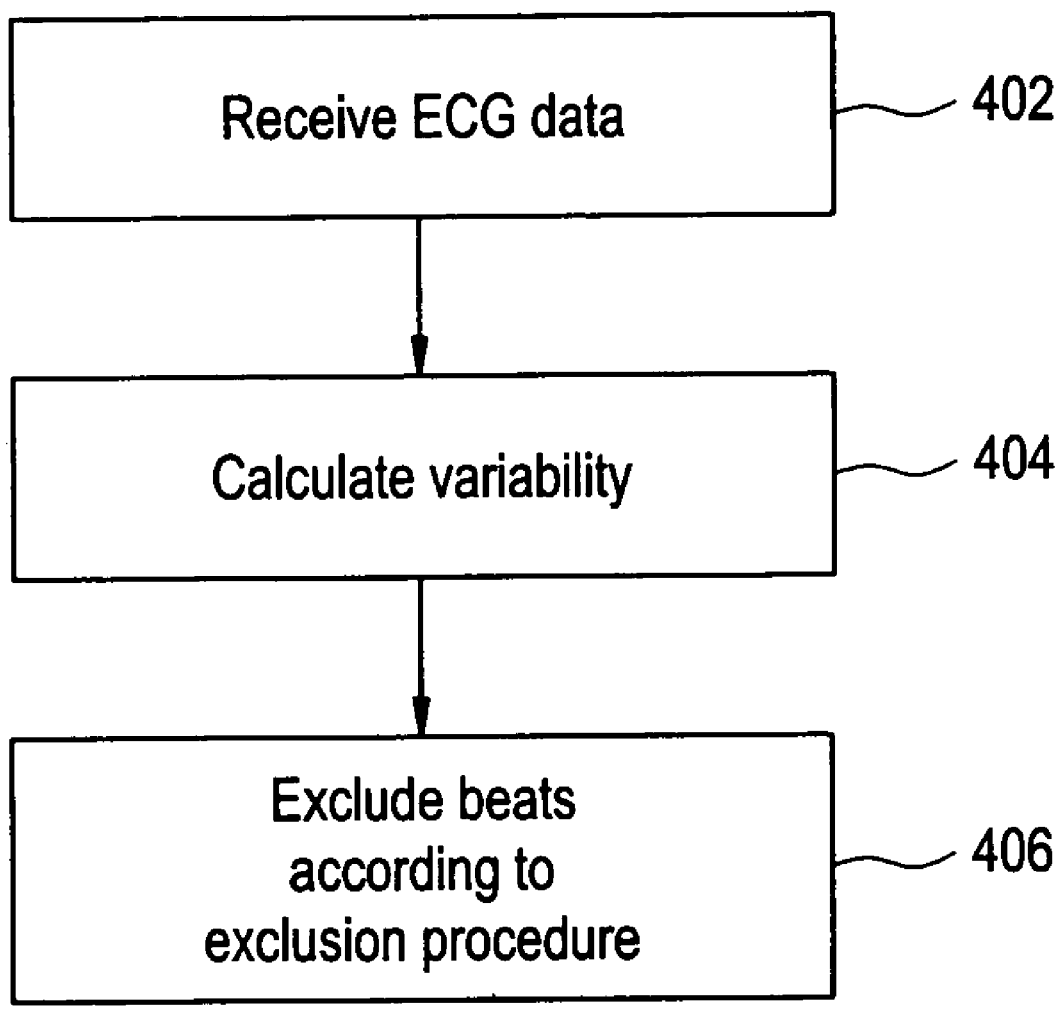

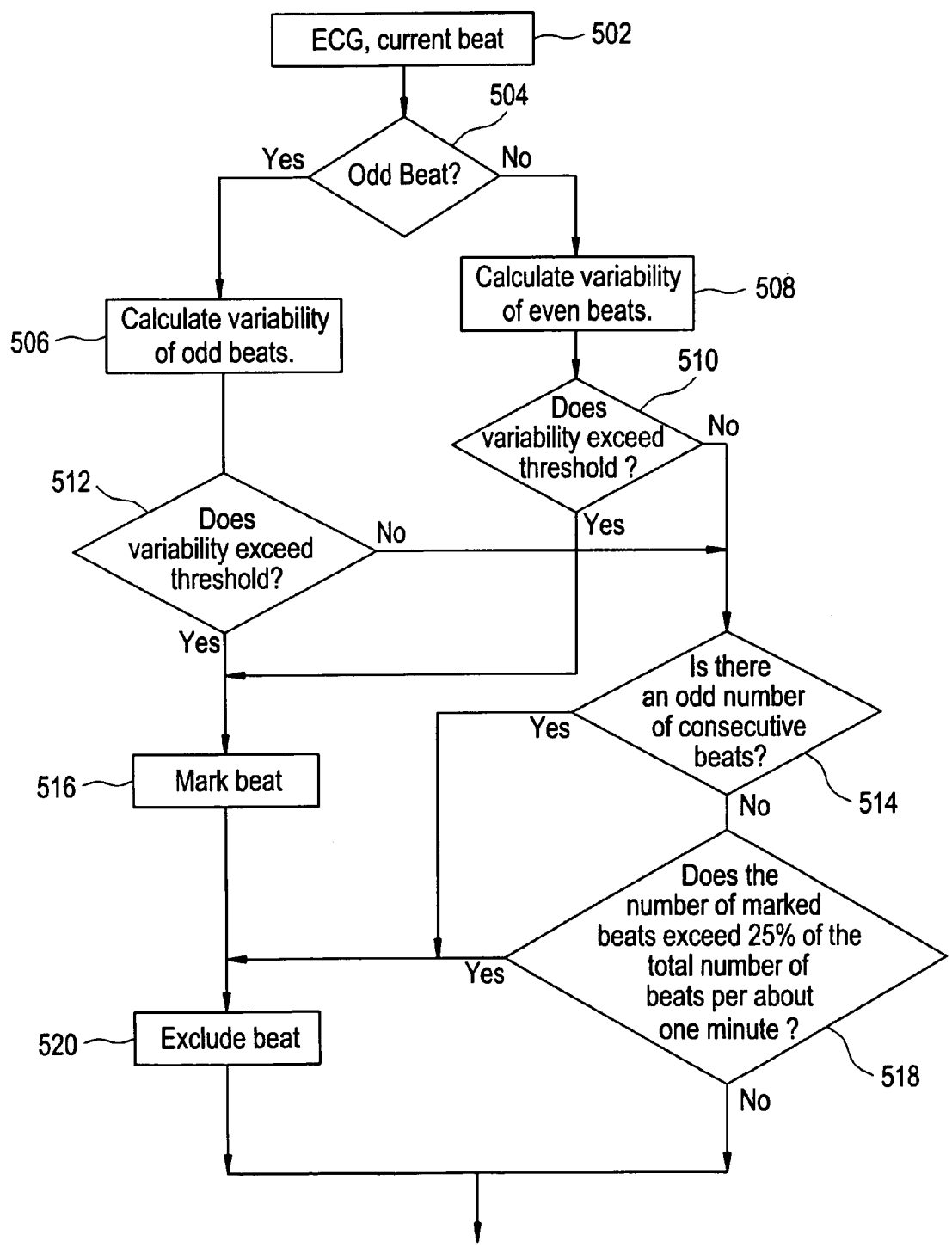

METHOD AND SYSTEM FOR IMPROVED MEASUREMENT OF T-WAVE ALTERNANS

BACKGROUND OF THE INVENTION

The field of the invention is cardiology. More particularly, the invention relates to a system and method for improving T-wave alternans measurements by excluding certain beats from calculations.

Electrical alternans are the differences in electrical potential at corresponding points between alternate heartbeats. T-wave alternans or alternation is a regular or beat-to-beat variation of the ST-segment or T-wave of an electrocardiogram (ECG) which repeats itself every two beats and has been linked to underlying cardiac instability. Typically, by enumerating all consecutive heart beats of a patient, beats with an odd number are referred to as "odd beats" and beats with an even number are referred to as "even beats." A patient's odd and even heartbeats may exhibit different electrical properties of diagnostic significance which can be detected by an ECG.

The presence of these electrical alternans is significant because patients at increased risk for ventricular arrhythmia's commonly exhibit alternans in the ST-segment and the T-wave of their ECG. Clinicians may therefore use these electrical alternans as a noninvasive marker of vulnerability to ventricular tacharrhythmias. The term T-wave alternans (TWA) is used broadly to denote electrical alternans such as these. It should be understood that the term encompasses both the alternans of the T-wave segment and the ST-segment of an ECG. U.S. Pat. No. 5,148,812 to Richard L Verrier and Bruce D. Nearing provides an example of a method of quantifying and measuring the magnitude of T-wave alternation in an ECG that can be performed non-invasively.

Determining the magnitude of T-wave alternation can oftentimes be difficult. TWA magnitudes are typically in the range of several microvolts to several hundred microvolts. These small amplitudes make the measurement and analysis of the TWA susceptible to noise. Noise sources such as white noise, motion artifacts caused by respiration or patient movement, noisy heart beats, premature beats and the like can skew TWA measurements.

During a stress test artifacts produced by the pedaling of a bicycle or by the footfalls on a treadmill can significantly disturb the measurement of T-wave alternans. Beats that are highly affected by these artifacts should be excluded from the recorded data, otherwise false positive T-wave alternans may be measured. In addition, when the heart rate approaches the footfall rate or the doubled pedaling rate the superimposed artifacts are difficult to discriminate from a real T-wave alternans. Because the heart rate increases continuously during a stress test, it is likely that the heart rate closely approximates the footfall or doubled pedaling rate for a certain time interval. Accordingly, additional beats must be excluded for a certain period of time after an episode of artifact. Thus, there exists a need to continuously measure the variability (or "variance") of odd beats and the variability of even beats and exclude specific beats from TWA calculations depending on the measured variability or previous episode of artifacts.

SUMMARY OF THE INVENTION

One embodiment of the present invention provides a method of measuring T-wave alternans in an ECG signal comprising the steps of receiving digitized ECG data including a plurality of alternating consecutive odd and even beats, calculating a variability for at least one odd or even beat wherein calculating the variability occurs continuously with each new beat, and excluding certain beats from T-wave alternans measurements according to an exclusion procedure.

Another embodiment of the present invention provides a method of measuring T-wave alternans in an ECG signal comprising the steps of receiving digitized ECG data where the digitized ECG data includes a plurality of alternating consecutive odd and even beats representing the ECG signal, calculating a variability for at least one odd or even beat, identifying a threshold limit, marking beats having a variability that exceeds the threshold limit to create marked odd beats and marked even beats, and excluding from T-wave alternans measurements certain beats. The beats that may be excluded from T-wave alternans measurements include at least one of the following beats: a marked odd beat, a marked even beat, and a beat consecutively following an odd number of excluded consecutive beats.

Another embodiment of the present invention provides a system for measuring T-wave alternans in an ECG signal comprising a means for receiving digitized ECG data including a plurality of alternating consecutive odd and even beats where the ECG data represents the ECG signal. Further, the system includes a means for calculating a variability for at least one odd or even beat continuously with each beat. The system also includes a means for identifying a threshold limit. The system includes a means for marking beats having a variability that exceeds the threshold limit to create marked odd beats and marked even beats. Furthermore, the system includes a means for excluding from T-wave alternans measurements at least one of the following beats: a marked odd beat, a marked even beat, and a beat consecutively following an odd number of excluded consecutive beats.

Another embodiment of the present invention provides a computer program product comprising a computer useable medium having computer program logic for enabling at least one processor in a computer system to measure T-wave alternans in an ECG signal. The computer program includes a means for enabling the at least one processor to receive digitized ECG data representing the ECG signal. Further, the computer program includes a means for enabling the at least one processor to calculate a variability for at least one odd or even beat continuously with each beat. In addition, the computer program includes a means for identifying a threshold limit and a means for marking beats having a variability that exceeds the threshold limit to create marked odd beats and marked even beats. The computer program also includes a means for excluding from T-wave alternans measurements at least one of the following beats: a marked odd beat, a marked even beat, and a beat consecutively following an odd number of excluded consecutive beats.

BRIEF DESCRIPTION OF THE DRAWINGS

FIG. 3 is a flow chart illustrating a method of measuring T-wave alternans according to an embodiment of the present invention.

FIG. 4 is a flow chart illustrating a method of measuring T-wave alternans according to an embodiment of the present invention.

FIG. 5 is a flow chart illustrating a method of measuring T-wave alternans according to an embodiment of the present invention.

DESCRIPTION OF THE PREFERRED EMBODIMENT

Figure 1A:
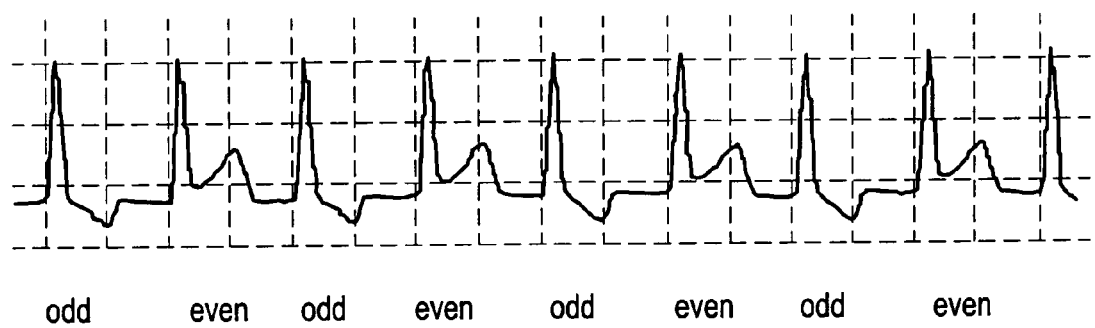
FIG. 1A is an example of a typical ECG plot over time showing odd and even beats.
Figure 1B:
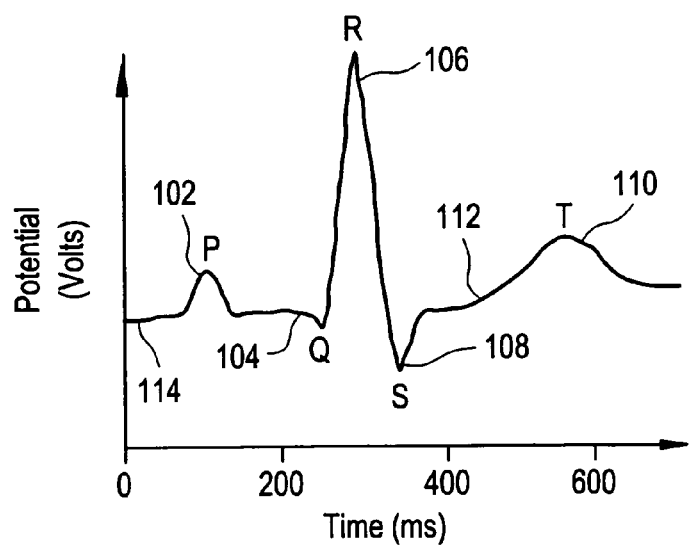
FIG. 1B is a portion of the ECG plot in FIG. 1A in greater detail.

FIGS. 1A and 1B provide an example of a human surface ECG 100. A deflection 102 is known as the "P-wave" and is due to excitation of the atria. Deflections 104, 106 and 108 are known as the "Q-wave," "R-wave," and "S-wave," respectively, and result from contraction (de-polarization) of the ventricles. Deflection 110 is known as the "T-wave" and is due to recovery (repolarization) of the ventricles.

A portion 112 of ECG 100 between the end of S-wave 108 and the beginning of T-wave 110 is known as the "ST segment." As used throughout this application, the term "T-wave" refers to and includes both the T-wave and the ST segment portions of the ECG.

Figure 2:
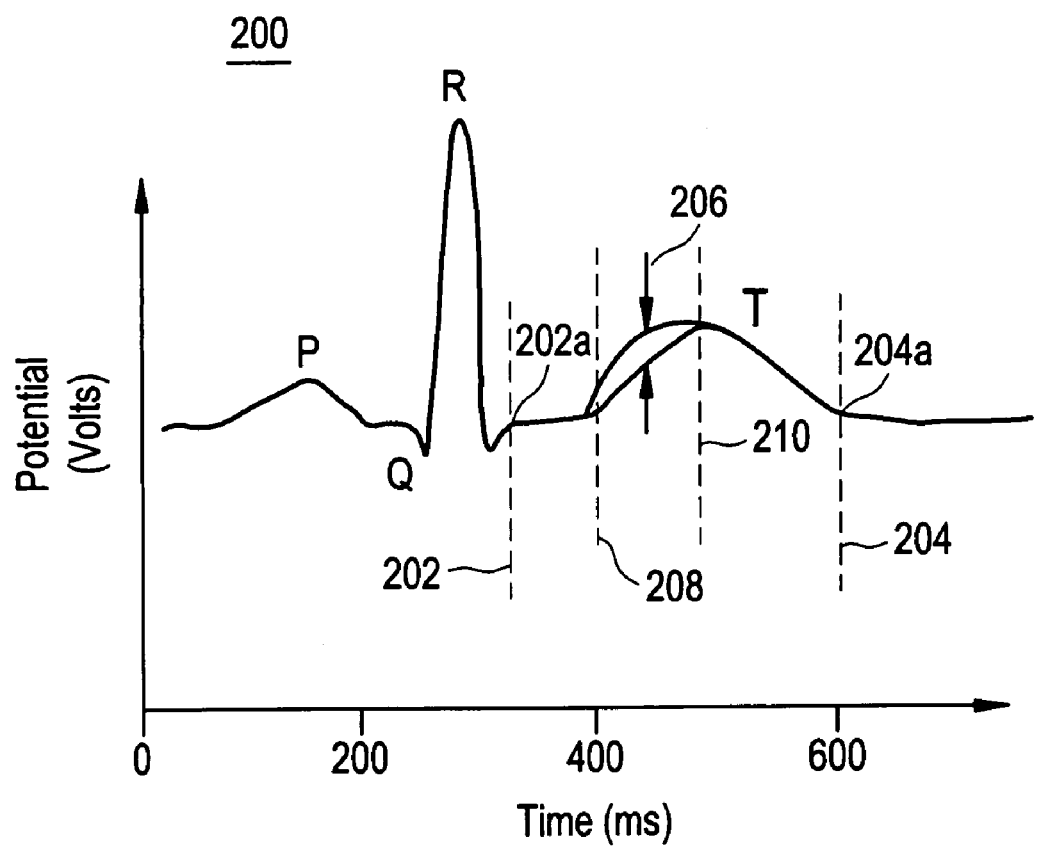
FIG. 2 is an ECG plot showing the superimposition of several beats to illustrate T-wave alternation.

T-wave alternans or alternation is a regular beat-to-beat variation of the T-wave of an ECG which repeats itself every two beats and has been linked to underlying cardiac electrical instability. FIG. 2 shows the concept of T-wave alternation for a sample precordial ECG signal 200. In ECG 200, several beats are superimposed upon one another to illustrate the alternans. Line 202 indicates the end of the QRS-complex, and line 204 indicates the end of the T-wave. Therefore, point 202a indicates $QRS_{end}$ and point 204a indicates $T_{end}$. The alternans is indicated at 206 as the divergence between the superimposed portions of the T-waves of successive beats. FIG. 2 shows an example of the alternation occurring primarily during the first half of the T-wave as illustrated between lines 208, 210.

FIG. 3 is a flow diagram representing a method 300 for improving measuring T-wave alternans in an ECG signal according to one embodiment of the present invention. Digitized ECG data including a plurality of odd and even beats is received from a patient at operation 302. In this embodiment, the ECG data represents the ECG signal. A variability is calculated for the odd or even beats at operation 304. A threshold limit is identified at operation 306. Beats are marked having a variability that exceeds a threshold limit to create marked odd beats and marked even beats at operation 308. Certain beats may be excluded from T-wave alternans measurements at operation 310, including a marked odd beat and/or a marked even beat, and a beat consecutively following an odd number of excluded consecutive beats.

According to a preferred embodiment of the present invention, calculation of a variability at operation 304 occurs continuously with each beat. Therefore, the calculation can occur in real-time so that information is processed with minimal delays. Further, calculating a variability at operation 304 includes determining the absolute value of the difference between the at least one odd or even beat and a respective prior consecutive odd or even beat in the ECG data. Thus, the variability for either the odd or even beats is calculated on the basis of differences between the ST-segment and T-wave areas from point $202a(QRS_{end})$ to point $204a(T_{end})$ of the last two consecutive odd or even QRS complexes. The variability for the beats is calculated with:

$$\text{var} = \frac{1}{T_{end} - QRS_{end}} \sum_{t=QRS_{end}}^{T_{end}} |S_0(t) - s_{-1}(t)|$$

where s0(t), s−1(t) are either: (a) a sample of a current odd QRS complex at position t and a sample of a previous odd QRS complex at position t, respectively, or (b) a sample of a current even QRS complex at position t and a sample of a previous even QRS complex at position t, respectively;

where var=variability;

where $T_{end}$=point at end of T-wave; and where $QRS_{end}$=point at end of QRS-complex.

It should be noted that this formula is either applied to the odd beats or the even beats, but not a combination and/or mixture of odd and even beats together.

All absolute values of the sample differences between current odd or even beat and the corresponding previous odd or even beat are summarized and then divided by the time distance between $T_{end}$ and $QRS_{end}$. The summarization starts at $QRS_{end}$ (point 202a) and ends at $T_{end}$ (point 204a). Alternatively, any number of methods may be used to calculate a variability at operation 304. For example, a standard deviation may be utilized, the average of the absolute values of the differences between a plurality of consecutive corresponding odd or even beats in the ECG data may be used, etc.

Once the variability is determined, the threshold is calculated and the variability is compared to it. This allows detection of QRS complexes superimposed by artifacts produced by pedaling, footfall, electrode manipulation, etc. In addition, the threshold allows for a certain tolerance in the variability among beats. Thus, beats will still be used when the variability is only considered slight or negligible. According to an embodiment of the present invention, the threshold is determined according to the following equation:

threshold=MIN(250µV, QRS-amplitude/4)

where V=volts;

where MIN=minimum of two values;

where QRS=QRS-complex; and where amplitude=maximal amplitude of the QRS-complex.

Determining the threshold may be done for both the odd beats and the even beats. The threshold determination disclosed here is merely exemplary and any number of thresholds may be used to measure the variability in the odd beats as well as in the even beats in an ECG signal. For example, the threshold may be determined by an experimental or empirical value, it may be given a constant value, etc. After calculating the variability and threshold, beats are excluded from T-wave alternans measurements as follows: (1) a marked odd beat; (2) a marked even beat; and (3) a beat consecutively following an odd number of excluded consecutive beats. The beats are excluded in step (3) to keep the odd/even order of the beats.

Method 300 may further include a step of excluding a new odd or new even beat from T-wave alternans measurements according to a holding function. According to one embodiment, the holding function comprises excluding a new odd or new even beat from T-wave alternans measurements where the total number of marked beats is in the range of about 10–100% of the total number of beats in the ECG data. More specifically, the holding function includes excluding a new odd or new even beat from T-wave alternans measurements where the total number of marked beats is greater than about 25% of the total number of beats in the ECG data. Alternatively, the holding function comprises excluding a new odd beat or new even beat from T-wave alternans measurements where the total number of marked beats is in the range of about 10–100% of about the last 40–85 beats in the ECG data. More particularly, the holding function includes excluding a new odd beat or new even beat from T-wave alternans measurements where the total number of marked beats is in the range of about 15–100% of about the last 64 beats in the ECG data. According to a preferred embodiment, the holding function includes excluding a new odd beat or new even beat from T-wave alternans measurements where the total number of marked beats is greater than about 25% of about the last 64 beats in the ECG data.

FIG. 4 is a flow diagram representing a method 400 of measuring T-wave alternans in an ECG signal according to one embodiment of the present invention. Digitized ECG data including a plurality of odd and even beats is received from a patient at operation 402. A variability is calculated continuously with each beat for the odd or the even beats at operation 404. Certain beats are excluded from T-wave alternans measurements according to an exclusion procedure at operation 406. The exclusion procedure may comprise the step of marking beats having a variability that exceeds a threshold limit. In addition, the exclusion procedure may include excluding from T-wave alternans measurements a marked odd beat, and/or a marked even beat, and a beat consecutively following an odd number of excluded consecutive beats. According to another embodiment, method 400 may comprise the step of excluding a new odd beat or new even beat from T-wave alternans measurements according to a holding function as described in method 300.

Referring to FIG. 5, the overall process 500 for measuring T-wave alternans in an ECG signal is shown. Process 500 can be carried out by a system such as a computer program or software product able to measure T-wave alternans in an ECG signal. First, the ECG data is received, including a current beat (odd or even) at operation 502. The process then determines whether the beat is odd at operation 504. If the beat is even, the process calculates the variability of even beats at operation 508. If the beat is odd, the process calculates the variability of odd beats at operation 506. At operations 510, 512, the process determines whether the beat exceeds the threshold. If the variability of the beats at operations 506 or 508 exceed the threshold, the beat is marked at operation 516. If the variability of the beats at operations 506, 508 do not exceed the threshold, the process determines if there is an odd number of excluded consecutive beats at operation 514. If there is an odd number of excluded consecutive beats, the beat is excluded from T-wave alternans measurements at operation 520. If there is not an odd number of excluded consecutive beats, the process determines whether the number of marked beats exceeds a value allowed according to a holding function at operation 518. Whether a beat is excluded according to a holding function is described above with respect to FIG. 3. Thus, FIG. 5 illustrates how the data is sorted continuously, in real-time with each beat. After operations 518, 520, beats will either be used in future T-wave alternans measurements, or they will be identified for exclusion from T-wave alternans computations. In addition to computer programs or software, the operations referred to in FIG. 5 may be carried out by any number of different methods. For example, each operation could be conducted manually by an operator, remotely by a user, over a network, etc.

While the embodiments and application of the invention illustrated in the figures and described above are presently preferred, it should be understood that these embodiments are offered by way of example only. Accordingly, the present invention is not limited to a particular embodiment, but extends to various modifications that nevertheless fall within the scope of this application.

What is claimed is:

1. A method of measuring T-wave alternans in an ECG signal comprising the steps of:
   receiving digitized ECG data including a plurality of alternating consecutive odd and even beats;
   calculating a variability for at least one odd or even beat, wherein calculating the variability occurs continuously with each new beat;
   excluding certain beats from T-wave alternans measurements according to an exclusion procedure; and
   excluding a new odd beat or new even beat from T-wave alternans measurements according to a holding function.

2. The method of claim 1, wherein the exclusion procedure comprises the step of marking beats having a variability that exceeds a threshold limit.

3. The method of claim 2, wherein the exclusion procedure further comprises excluding from T-wave alternans measurements at least one of the following beats:
   a marked odd beat;
   a marked even beat; and
   a beat consecutively following an odd number of excluded consecutive beats.

4. The method of claim 3, wherein the threshold is identified according to the following equation:

threshold=MIN(250μV, QRS-amplitude/4)

where V=volts;
where MIN=minimum of two values;
where QRS=QRS-complex; and
where amplitude=maximal amplitude of QRS-complex.

5. The method of claim 1, wherein the holding function comprises excluding a new odd beat or new even beat from T-wave alternans measurements where a total number of marked beats is greater than about 25% of a total number of beats per about one minute of the ECG data.

6. The method of claim 1, wherein the variability is calculated according the following equation:

$$\text{var} = \frac{1}{T_{end} - QRS_{end}} \sum_{t=QRS_{end}}^{T_{end}} |s_0(t) - s_{-1}(t)|$$

where $s_0(t)$, $s-1(t)$ are either: (a) a sample of a current odd QRS complex at position t and a sample of a previous odd QRS complex at position t, respectively, or (b) a sample of a current even QRS complex at position t and a sample of a previous even QRS complex at position t, respectively;
where var=variability;
where $T_{end}$=point at end of T-wave; and
where $QRS_{end}$=point at end of QRS-complex.

7. The method of claim 1, wherein the step of calculating a variability for at least one odd or even beat includes determining a standard deviation of at least one odd or even beat and a prior consecutive corresponding odd or even beat in the ECG data.

8. The method of claim 1, wherein the step of calculating a variability for at least one odd or even beat includes determining an average value of an absolute difference between a plurality of consecutive corresponding odd or even beats in the ECG data.

9. A method of measuring T-wave alternans in an ECG signal comprising the steps of:
receiving digitized ECG data including a plurality of alternating consecutive odd and even beats, the ECG data representing the ECG signal;
calculating a variability for at least one odd or even beat;
identifying a threshold limit;
marking beats having a variability that exceeds the threshold limit to create marked odd beats and marked even beats;
excluding from T-wave alternans measurements at least one of the following beats:
a marked odd beat;
a marked even beat; and
a beat consecutively following an odd number of excluded consecutive beat; and
excluding a new odd beat or new even beat from T-wave alternans measurements according to a holding function, wherein the step of calculating the variability occurs continuously with each beat.

10. The method of claim 9, wherein the threshold is identified according to the following equation:

threshold=MIN((constant value), (value calculated from QRS amplitude)).

11. The method of claim 10, wherein the threshold is identified according to the following equation:

threshold=MIN(250μV, QRS-amplitude/4)

where V=volts;
where MIN=minimum of two values;
where QRS=QRS-complex; and
where amplitude=maximal amplitude of QRS-complex.

12. The method of claim 9, wherein calculating the variability includes determining an absolute value of a difference between the at least one odd or even beat and a prior consecutive corresponding odd or even beat in the ECG data.

13. The method of claim 9, wherein the variability is calculated according the following equation:

$$\text{var} = \frac{1}{T_{end} - QRS_{end}} \sum_{t=QRS_{end}}^{T_{end}} |S_0(t) - s_{-1}(t)|$$

where so(t), s−1(t) are either: (a) a sample of a current odd QRS complex at position t and a sample of a previous odd QRS complex at position t, respectively, or (b) a sample of a current even QRS complex at position t and a sample of a previous even QRS complex at position t, respectively;
where var=variability;
where Tend=point at end of T-wave; and
where QRSend=point at end of QRS-complex.

14. The method of claim 9, wherein calculating the variability includes determining a standard deviation of at least one odd or even beat and a prior consecutive corresponding odd or even beat in the ECG data.

15. The method of claim 9, wherein calculating the variability includes determining an average value of an absolute difference between a plurality of consecutive corresponding odd or even beats in the ECG data.

16. The method of claim 9, wherein the holding function comprises excluding a new odd beat or new even beat from T-wave alternans measurements where a total number of marked beats is in a range of about 10–100% of a total number of beats in the ECG data.

17. The method of claim 9, wherein the holding function comprises excluding a new odd beat or new even beat from T-wave alternans measurements where a total number of marked beats is greater than about 25% of a total number of beats in the ECG data.

18. The method of claim 9, wherein the holding function comprises excluding a new odd beat or new even beat from T-wave alternans measurements where a total number of marked beats is in a range of about 10–100% of about 40–85 prior consecutive beats in the ECG data.

19. The method of claim 9, wherein the holding function comprises excluding a new odd beat or new even beat from T-wave alternans measurements where a totalnumber of marked beats is in a range of about 15–100% of about 64 prior consecutive 25 beats in the ECG data.

20. The method of claim 9, wherein the holding function comprises excluding a new odd beat or new even beat from T-wave alternans measurements where a total number of marked beats is greater than about 25% of about 64 prior consecutive beats in the ECG data.

21. The method of claim 9, wherein the holding function comprises excluding a new odd beat or new even beat from T-wave alternans measurements where a total number of marked beats is in a range of about 10–100% of a total number of beats per about 30–120 seconds in the ECG data.

22. The method of claim 9, wherein the holding function comprises excluding 10 a new odd beat or new even beat from T-wave alternans measurements where a total number of marked beats is greater than about 25% of a total number of beats per about one minute in the ECG data.

23. A system for measuring T-wave alternans in an ECG signal comprising:
means for receiving digitized ECG data including a plurality of alternating consecutive odd and even beats, the, ECG data representing the ECG signal;
means for calculating a variability for at least one odd or even beat continuously with each beat;
means for identifying a threshold limit;
means for marking beats having a variability that exceeds the threshold limit to create marked odd beats and marked even beats; and
means for excluding from T-wave alternans measurements at least one of the following beats:
a marked odd beat;
a marked even beat; and
a beat consecutively following an odd number of excluded consecutive beats.

24. The system of claim 23, wherein the means for calculating the variability includes determining an absolute value of a difference between the at least one odd or even beat and a prior consecutive corresponding odd or even beat in the ECG data.

25. The system of claim 24, further comprising a means for excluding a new odd beat or new even beat from T-wave alternans measurements according to a holding function.

26. The system of claim 25, wherein the holding function excludes a new odd beat or new even beat from T-wave alternans measurements where a total number of marked beats is in a range of about 10–100% of a total number of beats in the ECG data.

27. The system of claim 25, wherein the holding function excludes a new odd beat or new even beat from T-wave alternans measurements where a total number of marked beats is greater than about 25% of a total number of beats in the ECG data.

28. The system of claim 25, wherein the holding function excludes a new odd beat or new even beat from T-wave alternans measurements where a total number of marked beats is in a range of about 10–100% of about 40–85 prior consecutive beats in the ECG data.

29. The system of claim 25, wherein the holding function excludes a new odd beat or new even beat from T-wave alternans measurements where a total number of marked beats is in a range of about 15–100% of about 64 prior consecutive beats in the ECG data.

30. The system of claim 25, wherein the holding function excludes a new odd beat or new even beat from T-wave alternans measurements where a total number of marked beats is greater than about 25% of about 64 prior consecutive beats in the ECG data.

31. The system of claim 25, wherein the holding function excludes a new odd beat or new even beat from T-wave alternans measurements where a total number of marked beats is in a range of about 10–100% of a total number of beats per about 30–120 seconds in the ECG data.

32. The system of claim 25, wherein the holding function excludes a new odd beat or new even beat from T-wave alternans measurements where a total number of marked beats is greater than about 25% of a total number of beats per about one minute in the ECG data.

33. A computer program product comprising a computer useable medium having computer program logic for enabling at least one processor in a computer system to measure T-wave alternans in an ECG signal, said computer program logic comprising:
 means for enabling the at least one processor to receive digitized ECG data representing the ECG signal;
 means for enabling the at least one processor to calculate a variability for at least one odd or even beat continuously with each beat;
 means for identifying a threshold limit;
 means for marking beats having a variability that exceeds the threshold limit to create marked odd beats and marked even beats; and
 means for excluding from T-wave alternans measurements at least one of the following beats:
  a marked odd beat;
  a marked even beat; and
  beat consecutively following an odd number of excluded consecutive beats.

34. The computer program product of claim 33, wherein the means for calculating the variability includes determining an absolute value of a difference between the at least one odd or even beat and a prior consecutive corresponding odd or even beat in the ECG data.

35. The computer program product of claim 33, further comprising a means for excluding a new odd beat or new even beat from T-wave alternans measurements according to a holding function, the holding function excluding a new odd beat or new even beat from T-wave alternans measurements where a total number of marked beats is greater than about 25% of about 64 prior consecutive beats in the ECG data.

* * * * *